US012789000B2

(12) United States Patent
Victorine et al.

(10) Patent No.: US 12,789,000 B2
(45) Date of Patent: Nov. 10, 2026

(54) BIOSTIMULATOR HAVING A STRAIN-RELIEVED PACING ELEMENT

(71) Applicant: Pacesetter, Inc., Sylmar, CA (US)

(72) Inventors: Keith Victorine, Valencia, CA (US); Kyle J. Nix, Arcadia, CA (US); Daniel Kwon, Los Angeles, CA (US); Steve Chantasirivisal, Santa Clarita, CA (US)

(73) Assignee: Pacesetter, Inc., Sylmar, CA (US)

(*) Notice: Subject to any disclaimer, the term of this patent is extended or adjusted under 35 U.S.C. 154(b) by 127 days.

(21) Appl. No.: 18/667,952

(22) Filed: May 17, 2024

(65) Prior Publication Data

US 2024/0390689 A1 Nov. 28, 2024

Related U.S. Application Data

(60) Provisional application No. 63/468,230, filed on May 22, 2023.

(51) Int. Cl.
*A61N 1/375* (2006.01)
*A61N 1/362* (2006.01)

(52) U.S. Cl.
CPC ........... *A61N 1/3756* (2013.01); *A61N 1/362* (2013.01); *A61N 1/37512* (2017.08); *A61N 1/37518* (2017.08); *A61N 1/3758* (2013.01)

(58) Field of Classification Search
CPC .. A61N 1/3756; A61N 1/362; A61N 1/37512; A61N 1/37518; A61N 1/3758; A61N 1/372; A61N 1/3621; A61N 1/37252
See application file for complete search history.

(56) References Cited

U.S. PATENT DOCUMENTS

| | | | | |
|---|---|---|---|---|
| 2010/0082086 | A1* | 4/2010 | Zhu | A61N 1/0558 607/116 |
| 2010/0331938 | A1* | 12/2010 | Sommer | A61N 1/0534 607/116 |
| 2012/0191169 | A1* | 7/2012 | Rothstein | A61N 1/0573 607/127 |
| 2018/0264274 | A1* | 9/2018 | Haasl | A61N 1/059 |
| 2020/0289835 | A1 | 9/2020 | Eby et al. | |
| 2020/0306530 | A1 | 10/2020 | Koop et al. | |
| 2020/0306547 | A1* | 10/2020 | Liu | A61N 1/37518 |
| 2021/0046306 | A1 | 2/2021 | Grubac et al. | |
| 2021/0085957 | A1 | 3/2021 | Foster et al. | |

(Continued)

OTHER PUBLICATIONS

Extended European Search Report for related EP Application No. 24176914.0 mailed on Jul. 1, 2024, 7 pages.

(Continued)

*Primary Examiner* — Paula J Stice
(74) *Attorney, Agent, or Firm* — WOMBLE BOND DICKINSON (US) LLP

(57) ABSTRACT

A biostimulator includes a housing having a longitudinal axis and containing an electronics compartment. The biostimulator includes a fixation element coupled to the housing. The fixation element extends about the longitudinal axis. The biostimulator includes a pacing element coupled to the housing. The pacing element includes a strain relief surrounding a flexible conductor distal to the fixation element. A stiffness of the strain relief decreases in a distal direction. Other embodiments are also described and claimed.

18 Claims, 11 Drawing Sheets

(56) References Cited

U.S. PATENT DOCUMENTS

| | | | | |
|---|---|---|---|---|
| 2021/0228888 | A1 * | 7/2021 | Zhang .................. | A61N 1/3756 |
| 2023/0191121 | A1 | 6/2023 | Bornzin et al. | |

OTHER PUBLICATIONS

Extended European Search Report dated Apr. 16, 2026 from related European Patent Application No. 26159591.2, 8 pages.

Communication under Rule 71(3) EPC (intent to grant) dated Nov. 14, 2025 from related European Patent Application No. 24176914.0, 8 pages.

* cited by examiner

BIOSTIMULATOR HAVING A STRAIN-RELIEVED PACING ELEMENT

This application claims the benefit of priority of U.S. Provisional Patent Application No. 63/468,230, filed on May 22, 2023, titled "Biostimulator Having Strain-Relieved Pacing Element," which is incorporated herein by reference in its entirety to provide continuity of disclosure.

BACKGROUND

Field

The present disclosure relates to biostimulators. More specifically, the present disclosure relates to leadless biostimulators useful for deep septal pacing.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Leadless cardiac pacemakers incorporate electronic circuitry at the pacing site and eliminate leads, thereby avoiding shortcomings associated with conventional cardiac pacing systems. Leadless cardiac pacemakers can be anchored at the pacing site, e.g., in a right ventricle and, for dual-chamber pacing, in a right atrium, by an anchor.

Cardiac pacing of the His-bundle is clinically effective and advantageous by providing a narrow QRS affecting synchronous contraction of the ventricles. His-bundle pacing in or near a membranous septum of a heart, however, has some drawbacks. The procedure is often long in duration and requires significant fluoroscopic exposure. Furthermore, successful His-bundle pacing cannot always be achieved. Pacing thresholds are often high, sensing is challenging, and success rates can be low.

Deep septal pacing is an alternative to His-bundle pacing. Deep septal pacing involves pacing past the His-bundle toward the right ventricle apex. More particularly, deep septal pacing targets the left bundle branch below the His site. Deep septal pacing has been achieved using a lead in which the electrode penetrates several millimeters into the septum. Pacing thresholds associated with deep septal pacing are potentially lower than with His-bundle pacing, and clinical efficacy of the approach has been demonstrated.

SUMMARY

Existing pacing leads are not well suited to pacing the deep septal area. Deep septal pacing, e.g., left bundle branch area pacing (LBBAP) can require a pacing electrode to penetrate through a majority of a ventricular septal wall to extend into the left bundle branch or into a left bundle fascicular that resides on a left side of a septum. More particularly, the pacing electrode may be required to penetrate 7-15 mm into the ventricular septal wall. Existing pacing leads lack the ability to control penetration into the target tissue and are susceptible to buckling. Thus, the leads may not penetrate beyond the fibrous endocardial tissue. In addition to deep penetration, an effective LBBAP lead may require several attempts at placement before the target region is engaged. Accordingly, there is a need for a leadless biostimulator having a pacing element configured to reach the deep septal area without buckling for deep septal pacing of a heart, and which can be deployed several times to find an acceptable location for the pacing element.

A biostimulator is described. In an embodiment, the biostimulator includes a housing having a longitudinal axis. The housing contains an electronics compartment. The biostimulator includes a fixation element coupled to the housing. The fixation element extends about the longitudinal axis. The biostimulator includes a pacing element coupled to the housing. The pacing element includes a strain relief surrounding a flexible conductor. A stiffness of the strain relief decreases in a distal direction.

A biostimulator is described. In an embodiment, the biostimulator includes a housing having a longitudinal axis. The housing contains an electronics compartment. The biostimulator includes a pacing element coupled to the housing. The pacing element includes a flexible conductor extending between the electronics compartment and a distal pacing tip. The biostimulator includes a strain relief surrounding the flexible conductor. A stiffness of the strain relief decreases in a distal direction.

A biostimulator is described. In an embodiment, the biostimulator includes a housing having a longitudinal axis. The housing contains an electronics compartment. The biostimulator includes a fixation element mount coupled to the housing. The fixation element mount has a tapered outer mount surface. The biostimulator includes a fixation element partly embedded in the fixation element mount radially inward of the tapered outer mount surface. The fixation element extends helically about the longitudinal axis.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Figure 1:
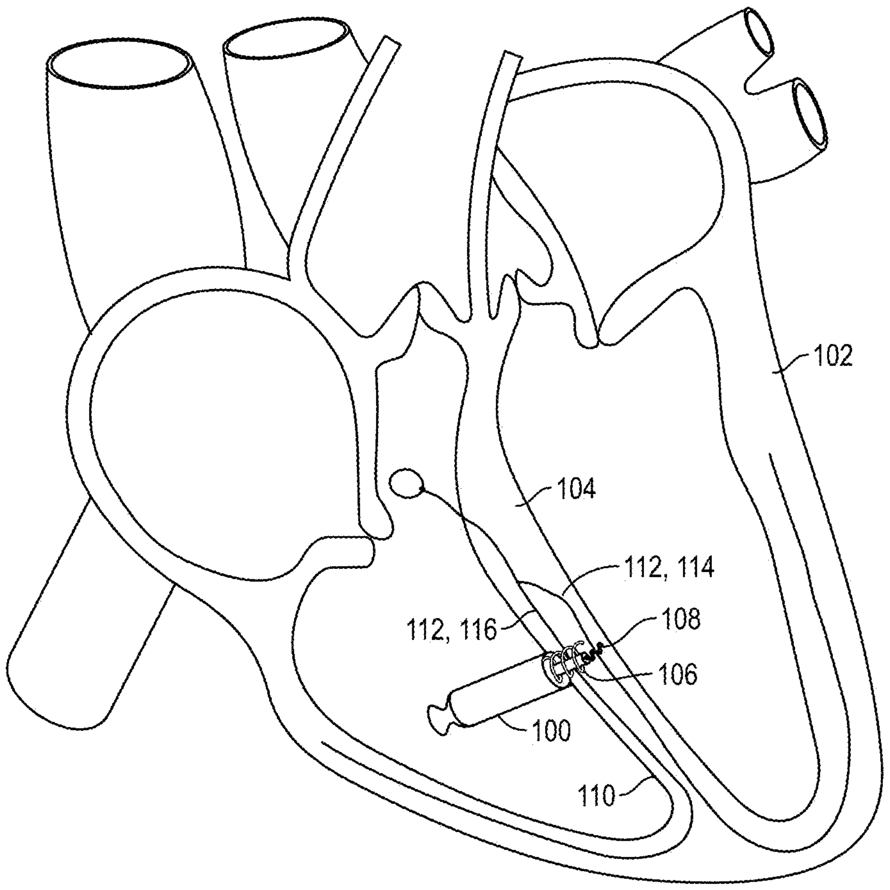
FIG. 1 is a diagrammatic cross section of a patient heart illustrating an example implantation of a biostimulator in a target anatomy, in accordance with an embodiment.

Embodiments describe a biostimulator, such as a leadless pacemaker, having a strain-relieved pacing element that extends distal to a fixation element. As described below, the biostimulator can be used to perform deep septal pacing of a heart. The biostimulator may, however, be used in other applications, such as deep brain stimulation. Thus, reference to the biostimulator as being a cardiac pacemaker for deep septal pacing is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator for deep septal pacing includes a strain-relieved pacing element. More particularly, the pacing element can include a flexible conductor surrounded or encapsulated by a strain relief. The flexible conductor can extend distally and convey pacing impulses to a tip electrode configured to be deeply implanted in a heart septum, e.g., 7-20 mm deep. The flexible conductor can be shrouded by the strain relief that supports the flexible conductor. More particularly, the strain relief can have a stiffness that decreases in a distal direction to impart column strength that resists buckling and allows the pacing element to be driven toward the target region, e.g., a left bundle branch. The strain relief may incorporate stiffening elements, such as a tubular braid, to add stiffness and reduce a likelihood of fatigue failure. The strain relief can also allow for lateral deflection of the flexible conductor. The pacing element can therefore penetrate the septal tissue to deliver the distal tip to the target region and may also flex to allow a housing of the biostimulator to move within a heart chamber without unduly stressing the target tissue. In an aspect, the biostimulator includes a fixation element to removably attach a housing of the biostimulator to the target tissue. The fixation element can be detached and reattached to the target tissue to allow the biostimulator to be deployed several times to engage the target region.

Referring to FIG. 1, a diagrammatic cross section of a patient heart illustrating an example implantation of a biostimulator in a target anatomy is shown in accordance with an embodiment. A leadless biostimulator system, e.g., a cardiac pacing system, includes one or more biostimulators 100. The biostimulators 100 can be implanted in a patient heart 102, and can be leadless (and thus, may be leadless cardiac pacemakers). Each biostimulator 100 can be placed in a cardiac chamber, such as a right atrium and/or right ventricle of the heart 102, or attached to an inside or outside of the cardiac chamber. For example, the biostimulator 100 can be attached to a septum 104 of the heart 102. More particularly, the biostimulator 100 can be delivered to the septum 104, and one or more elements, such as a fixation element 106 and/or a pacing element 108 can pierce a septal wall 110 of the septum 104 to engage and anchor the biostimulator 100 to the tissue. In a particular embodiment, the biostimulator 100 can use two or more electrodes located on or within a housing of the biostimulator 100 for pacing the cardiac chamber upon receiving a triggering signal from at least one other device within the body. In an embodiment, one or more of the fixation element 106 or the pacing element 108 is an active electrode.

Leadless pacemakers or other leadless biostimulators 100 can be delivered to or retrieved from a patient using delivery or retrieval systems. The leadless biostimulator system can include delivery or retrieval systems, which may be catheter-based systems used to carry a leadless biostimulator 100 intravenously to or from a patient anatomy. The delivery or retrieval systems may be referred to collectively as transport systems. In some implementations of transport systems, a leadless pacemaker is attached or connected to a distal end of a catheter and advanced intravenously into or out of the heart 102. The transport system can include features to engage the leadless pacemaker to allow fixation of the leadless pacemaker to tissue. For example, in implementations where the leadless pacemaker includes an active engaging mechanism, such as a fixation element 106, the transport system can include a docking cap or key at a distal end of the catheter, and the docking cap or key may be configured to engage the leadless pacemaker and apply torque to screw the active engaging mechanism into or out of the tissue. In other implementations, the transport system includes clips designed to match the shape of a feature on the leadless pacemaker and apply torque to screw the active engaging mechanism into or out of the tissue.

When the biostimulator 100 is delivered to and screwed into the septum 104 of the heart 102, the pacing element 108 and/or the fixation element 106 may be positioned for deep septal pacing at respective bundle branches 112 in the septum 104. For example, an active electrode of the pacing element 108 can be positioned at the left bundle branch 114 in the septum 104. Similarly, the fixation element 106 can be positioned at the right bundle branch 116 in the septum 104. Optionally, one of the elements may be at a bundle branch and the other element may not be at a bundle branch.

Figure 2:
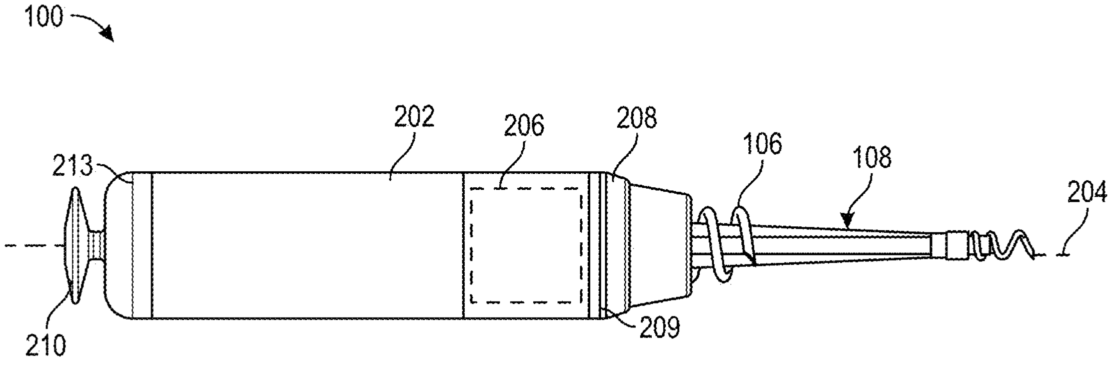
FIG. 2 is a side view of a biostimulator having a pacing element, in accordance with an embodiment.

Referring to FIG. 2, a side view of a biostimulator having a pacing element is shown in accordance with an embodiment. The biostimulator 100 can be a leadless cardiac pacemaker that can perform cardiac pacing and that has many of the advantages of conventional cardiac pacemakers while extending performance, functionality, and operating characteristics. The biostimulator 100 can have two or more electrodes, e.g., a portion of the pacing element 108 that acts as an active electrode and/or a portion of the fixation element 106 or a housing 202 that acts as an active electrode. The electrodes can deliver pacing pulses to bundle branches 112 within the septum 104 of the heart 102 to perform deep septal pacing, and optionally, can sense electrical activity from the muscle. The electrodes may also communicate bidirectionally with at least one other device within or outside the body.

In an embodiment, the biostimulator 100 includes the housing 202 having a longitudinal axis 204. The housing 202 can contain a primary battery to provide power for pacing, sensing, and communication, which may include, for example, bidirectional communication. The housing 202 can optionally contain an electronics compartment 206 (shown by hidden lines) to hold circuitry adapted for different functionality. For example, the electronics compartment 206 can contain circuits for sensing cardiac activity from the electrodes, circuits for receiving information from at least one other device via the electrodes, circuits for generating pacing pulses for delivery to tissue via the electrodes, or other circuitry. The electronics compartment 206 may contain circuits for transmitting information to at least one other device via the electrodes and can optionally contain circuits for monitoring device health. The circuit of the biostimulator 100 can control these operations in a predetermined manner. The biostimulator 100 can perform leadless pacing without a pulse generator located in the pectoral region or abdomen and/or without an electrode-lead separate from the pulse generator. The biostimulator 100 may also lack a communication coil or antenna, and may not have the substantial battery power required for transmitted communication through a communication coil or antenna.

Leadless pacemakers or other leadless biostimulators 100 can be fixed to an intracardial implant site, e.g., at the septal wall 110, by one or more actively engaging mechanisms or fixation mechanisms, such as a screw or helical member that screws into the myocardium. In an embodiment, the biostimulator 100 includes the fixation element 106 coupled to the housing 202. The fixation element 106 can include a helical fixation element and/or several tines, as described below. More particularly, the biostimulator 100 can include a header assembly having a flange 208 coupled to a distal housing end 209 of the housing 202, and the fixation element 106 can be coupled to and extend distal to the flange 208. The fixation element 106 can extend about the longitudinal axis 204. For example, in the case of a helical fixation element, the element can spiral about the longitudinal axis to a distal tip. In the case of a fixation element 106 having several tines, the tines can be arranged about the longitudinal axis and extend to respective distal tips. Accordingly, when the biostimulator 100 is delivered to the target tissue, the distal tip(s) of the fixation element 106 can pierce the tissue and the housing 202 can be rotated or pushed to affix the fixation element 106 to the target tissue.

In an embodiment, the biostimulator 100 includes an attachment feature 210. The attachment feature 210 can be mounted on a proximal housing end 213 of the housing 202. More particularly, the attachment feature 210 can be mounted on an opposite end of the housing 202 from the fixation element 106 and the pacing element 108, which as described above, can be coupled to the distal housing end 209 of the housing 202. The attachment feature 210 can facilitate precise delivery or retrieval of the biostimulator 100. For example, the attachment feature 210 can be formed from a rigid material to allow a transport system to engage the attachment feature 210 and transmit torque and/or axial loads to the attachment feature 210 to plunge the fixation element 106 or the pacing element 108 into the target tissue.

Figure 3:
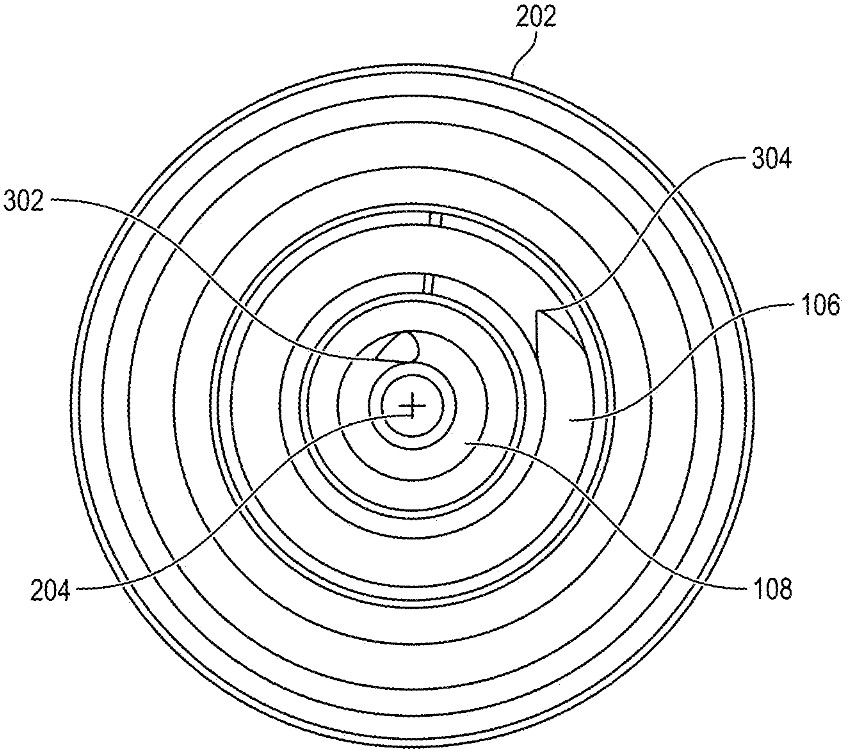
FIG. 3 is an end view of a biostimulator having a pacing element, in accordance with an embodiment.

Referring to FIG. 3, an end view of a biostimulator having a pacing element is shown in accordance with an embodiment. The biostimulator 100 can include the pacing element 108 coupled to the housing 202. The pacing element 108 can be coaxially arranged with the fixation element 106 about the longitudinal axis 204. More particularly, the pacing element 108 can extend along, e.g., axially along or helically about, the longitudinal axis 204 at a location that is radially inward from the fixation element 106. The pacing element 108 can extend distally to a distal tip having a distal pacing point 302. The distal pacing point 302 may be distal to the distal fixation tip 304. The pacing element 108 can include a helical element to screw into a target tissue or a conical element to pierce into the target tissue, as described below. Accordingly, when the fixation element 106 screws into or otherwise engages the target tissue, the pacing element 108 can also engage the tissue, and the housing 202 can be advanced and/or rotated to cause the distal pacing point 302 of the pacing element 108 to pierce the tissue and anchor the biostimulator 100.

One or more of the fixation element 106 or the pacing element 108 can be an active electrode, and can electrically communicate with the circuitry contained in the electronics compartment 206. Accordingly, the anchored element(s) can electrically communicate with the tissue and can transmit electrical pulses between the tissue and the circuitry of the biostimulator 100. To facilitate electrical function of the fixation element 106 and/or the pacing element 108, the element(s) may be coated in titanium nitride to reduce a polarization value of the electrode(s). By way of example, the titanium nitride coating may be in a range of 5 to 50 microns, e.g., 13 microns.

Figure 4:
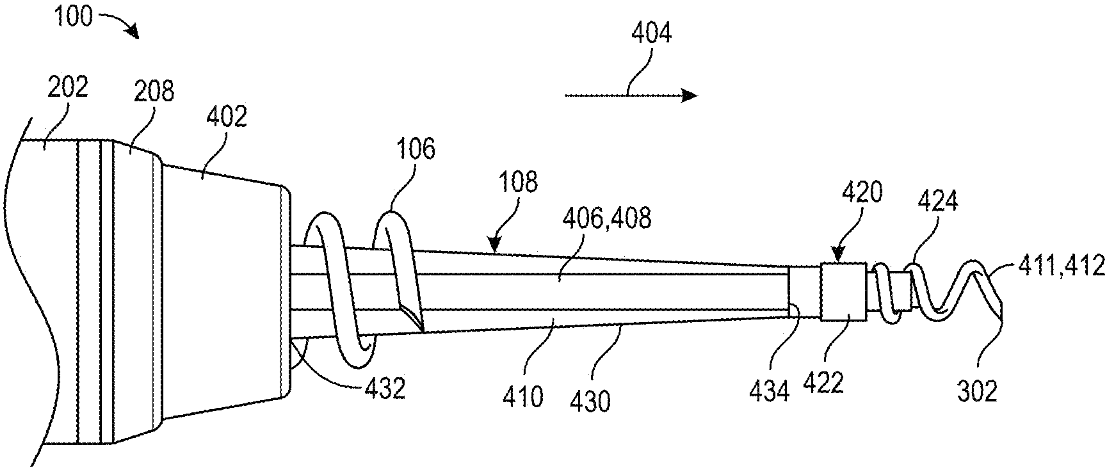
FIG. 4 is a side view of a distal portion of a biostimulator having a strain-relieved pacing element, in accordance with an embodiment.

Referring to FIG. 4, a side view of a distal portion of a biostimulator having a strain-relieved pacing element is shown in accordance with an embodiment. The biostimulator 100 can include a fixation element mount assembly includes the fixation element 106 mounted on a fixation element mount 402. The fixation element mount 402 can be non-conductive. For example, the fixation element mount 402 can be formed from polyether ether ketone (PEEK). The fixation element 106 can include MP35N wire having a wire diameter of 0.4-0.6 mm, e.g., 0.5 mm. The wire may be formed from a metal, such as stainless steel or a nickel cobalt alloy. The wire can be wrapped into several turns to form a helical fixation element. The turns can be screwed into the septum 104 to anchor the biostimulator 100 within the heart 102. The fixation element mount assembly is described in further detail below.

In an embodiment, the pacing element 108, which is coupled to the housing 202, extends in a distal direction 404 to the distal pacing point 302. More particularly, the pacing element 108 can include a flexible conductor 406 that extends between the electronics compartment 206 and the distal pacing point 302. The flexible conductor 406 can include a conductive lead extending in the distal direction 404 through the fixation element mount 402 and the fixation element 106 to the distal pacing point 302 distal to the distal fixation tip 304. The flexible conductor 406 can be electrically connected to the distal pacing point 302. For example, in an embodiment, the flexible conductor 406 includes a conductive cable 408 having one or more strands formed from an electrically conductive material to convey pacing impulses from circuitry within the electronics compartment 206 to the distal pacing point 302.

In an embodiment, the pacing element 108 of the biostimulator 100 includes a strain relief 410 surrounding, e.g., encapsulating, the flexible conductor 406. More particularly, the strain relief 410 can cover and/or surround the flexible conductor 406. The strain relief 410 can insulate a length of the pacing element 108. For example, the flexible conductor 406 can be encapsulated by the strain relief 410 over its length, including over a portion of the flexible conductor distal to the fixation element 106. The strain relief 410 can electrically insulate and mechanically support the flexible conductor 406, as described below.

In an embodiment, the pacing element 108 includes a distal tip 411. The distal tip 411 can include a helical electrode 412. The helical electrode 412 can include an elongated screw. More particularly, the pacing element 108 can include the helical electrode 412 extending about the longitudinal axis 204 to the distal pacing point 302. In an embodiment, the pacing element 108 helix includes platinum-iridium wire (e.g., 90-10 wire) having a diameter of 0.25-0.31 mm, e.g., 0.28 mm diameter. A major diameter of the helix can be 1.2-1.6 mm, e.g., 1.4 mm.

The pacing element 108 can extend distal to the fixation element mount 402 by a length sufficient for the distal tip 411 of the pacing element 108 to access the target region, e.g., the left bundle branch 114. The left bundle branch 114 may be at a depth of 10-25 mm from the septal wall 110, typically. Accordingly, the pacing element 108 can have a length of 7-20 mm, e.g., 12 mm or 16 mm, from a distal end of the fixation element mount 402 to the distal pacing point 302. Accordingly, the pacing element 108 can provide a means of pacing a target tissue that is distal to tissue being engaged by the fixation element 106. For example, the pacing element 108 can pace the left bundle branch 114 when the fixation element 106 is engaged near a surface of the septal wall 110 and/or near the right bundle branch 116.

In an embodiment, the fixation element mount 402 can engage the septal wall 110 to stabilize the biostimulator 100 and provide some depth control for the pacing element 108. For example, the fixation element mount 402 can partially burrow into the septal tissue, which can create some resistance between the septal tissue and the fixation element mount 402. The resistance can secure the fixation element mount 402 within the target site. Furthermore, the burrowing action can allow the pacing element 108 to advance further into the target tissue, e.g., toward the left bundle branch 114. Accordingly, the fixation element mount 402 can plunge into the target tissue to locate the pacing element 108 at the pacing site.

The helical electrode 412 may be mounted on a tip support 420. The tip support 420 can include a base 422, which may be bonded to or crimped on to the flexible conductor 406. A boss 424 can extend distally from the base 422. The boss 424 may have an outer diameter that is less than an outer diameter of base 422. The boss 424 may be inserted into an inner channel of the distal pacing element 108, e.g., the helical electrode 412. The distal tip 411 may be secured to the tip support 420, e.g., by welding the distal tip 411 to the base 422 or the boss 424. Accordingly, the distal tip 411 can be secured to the flexible conductor 406 to receive and relay pacing impulses to the target tissue at the distal pacing point 302.

The strain relief 410 of the pacing element 108 supports the flexible conductor 406 to provide sufficient stiffness to the pacing element 108 to penetrate the tissue. The strain relief 410 nonetheless, is flexible enough to resiliently bend under tissue movement and therefore not damage the tissue. Accordingly, the strain relief 410 can have a stiffness that decreases in a distal direction to provide a proximal section that is stiffer than a distal section. The proximal section can support tissue penetration and the distal section can flex resiliently. The stiffness transition between the proximal end and the distal end of the strain relief may occur discretely, e.g., in a stepwise manner, or gradually, e.g., continuously. For example, the strain relief can have a tapered outer surface or other structural characteristics, as described below, to achieve a distally decreasing stiffness profile.

In an embodiment, the pacing element 108 has an outer diameter in a range of 2-5 French. In such an embodiment, an outer surface 430 of the strain relief 410 can taper radially inward in the distal direction 404 from a proximal location 432 to a distal location 434. The proximal location 432 can be a longitudinal location on the outer surface 430 at a same longitudinal position as the distal end of the fixation element mount 402. The distal location 434 on the outer surface 430 can be a distalmost point of the strain relief 410, adjacent to the tip support 420. In an embodiment, a diameter of the outer surface 430 at the proximal location 432 is larger than a diameter of the outer surface 430 at the distal location 434.

The pacing element stiffness can balance high column strength to facilitate plunging or screwing the pacing element 108 into the ventricular septal wall 110 without buckling, against flexibility to yield under significant side loads applied to the distal tip 411 (or bending moments caused by loads applied to the distal tip 411 and the attachment feature 210). For example, the pacing element 108 can be stiff enough to engage tissue to enter perpendicularly into the septum 104, however, the housing 202 may be deflected off axis relative to the pacing element 108, e.g., by being angled down through a heart valve when the pacing element 108 is engaging tissue, without damaging the target tissue.

In an embodiment, the strain relief 410 is formed from a flexible, insulative material, such as polyurethane, silicone, or combinations thereof. For example, the strain relief 410 may be formed from a co-polymer insulation made of a combination of polyurethane and silicone. The strain relief 410 may be formed as a layer of material having a thickness of 0.005-0.020 inch, e.g., 0.010 inch. The strain relief 410 can be thick enough to support the flexible conductor 406 without increasing a dimension of the pacing element 108 significantly. For example, the strain relief 410 thickness may be equal to or less than a diameter of the flexible conductor 406.

The strain relief 410 may be formed from a single material having a consistent hardness. The tapered outer surface of the consistent material can provide therefore provide a continuously varying cross-sectional area that results in a distally decreasing stiffness profile. Alternatively, the strain relief 410 may be formed from material(s) of different hardness combined to provide the decreasing stiffness profile. For example, several tubular sections having different hardness (and optionally, same cross-sectional areas) may be fused to form a single strain relief tube having a transition in hardness from a stiffer material at a proximal end to less stiff material at a distal end. The transitions may be discrete or gradual based on the fusion process. It will be appreciated that the transition in stiffness of such a tubular strain relief can be achieved without tapering the outer surface of the strain relief.

Figure 5:
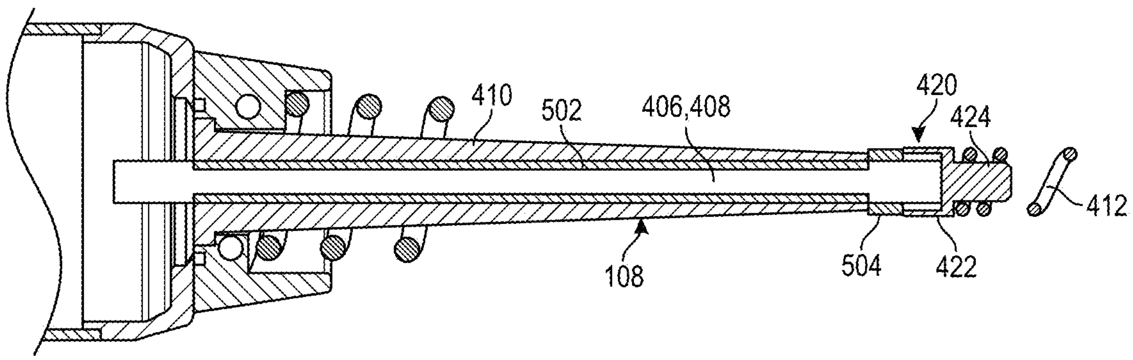
FIG. 5 is a side view of a distal portion of a biostimulator having a strain-relieved pacing element, in accordance with an embodiment.

Referring to FIG. 5, a side view of a distal portion of a biostimulator having a strain-relieved pacing element is shown in accordance with an embodiment. The flexible conductor 406 can include a straight or coiled wire. In an embodiment, the flexible conductor 406 includes the conductive cable 408, which may be a stranded cable centrally located and extending along the longitudinal axis 204. The conductive cable 408 may be formed from several wire strands that are coiled or woven to form a flexible cable structure. The flexible conductor 406 may, for example, have a diameter of 0.007-0.040 inch, e.g., 0.010 inch. The cable diameter, angles of the wire strands, and other cable structural characteristics may be adjusted to tune the column strength of the pacing element 108. For example, the cable diameter may be increased to achieve a predetermined column strength when a longer pacing element 108 is used. By contrast, the cable diameter may be decreased to achieve the predetermined column strength when the pacing element 108 is shorter.

In an embodiment, the pacing element 108 includes an intermediate insulation sleeve 502 between the flexible conductor 406 and the strain relief 410. The insulation sleeve 502 may, for example, include a polymer tube separating at least a portion of the flexible conductor 406 from the strain relief 410. The insulation sleeve 502 can be formed from an insulative polymer such as a fluorine-based plastic, e.g., ethylene tetrafluoroethylene. Accordingly, pacing impulses delivered through the flexible conductor 406 can be insulated from a surrounding tissue within which the strain relief 410 is located. The pacing impulses can therefore be delivered through the flexible conductor 406 to the pacing tip to pace the target tissue.

In an embodiment, the biostimulator 100, and more particularly the pacing element 108, is coupled to a therapeutic agent. For example, a monolithic controlled release device (MCRD) 504 may be mounted on the pacing element 108. The MCRD 504 includes a material, e.g., a silicone matrix, containing a therapeutic agent, which may be eluted into a surrounding tissue. The MCRD 504 can have a tubular structure with a central lumen to receive the flexible conductor 406 and an outer surface facing outward toward a surrounding environment. The MCRD 504 can therefore form a collar around the flexible conductor 406. The MCRD 504 may be located proximal or distal to the base 422 of the tip support 420. For example, the MCRD 540 is shown proximal to the base 422 in FIG. 5, however, the MCRD 504 may form a collar around the boss 424 of the tip support 420, in an embodiment.

The MCRD 504 can include the therapeutic material, which may include a corticosteroid, such as dexamethasone sodium phosphate, dexamethasone acetate, etc. Furthermore, the therapeutic agent can be loaded in the silicone matrix. Accordingly, the MCRD 504 can deliver a specified dose of the therapeutic agent into the target tissue, to reduce inflammation or injury of the target tissue that the pacing element 108 engages.

In addition to or instead of the MCRD 504, the biostimulator 100 may include a surface coating to provide therapeutic action. For example, a therapeutic agent, such as those described above or alternative therapeutic agents, e.g., Everolimus, may be coated on one or more components of the biostimulator 100. The coating may be applied by spray coating or another coating methodology. In an embodiment, Everolimus is coated on an outer surface of the pacing element 108, such as on the strain relief 410, the helical electrode 412, etc. The Everolimus (and/or other therapeutic agent) may be embedded in a coating matrix. For example, the Everolimus may be embedded in a fluoropolymer matrix. Therapeutic action of the therapeutic agent may be tuned through adjustments to the matrix composition that achieve a predetermined time release.

Figure 6:
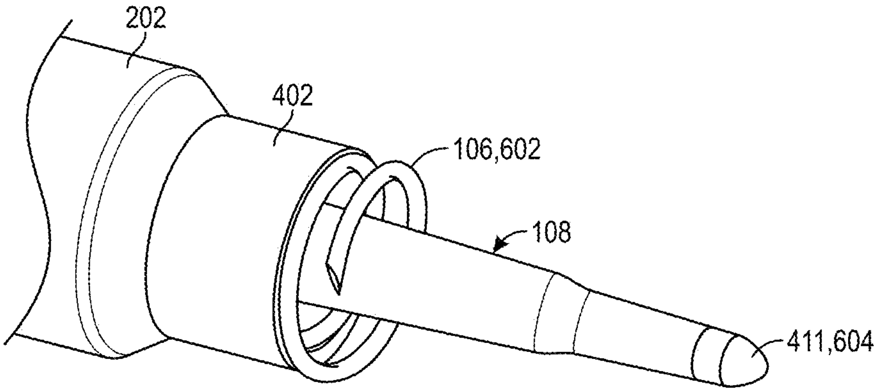
FIG. 6 is a perspective view of a distal portion of a biostimulator having a strain-relieved pacing element, in accordance with an embodiment.

Referring to FIG. 6, a perspective view of a distal portion of a biostimulator having a strain-relieved pacing element is shown in accordance with an embodiment. The pacing element 108 and the fixation element 106 may have a same or different mode of tissue penetration. In an embodiment, the fixation element 106 includes a helical fixation element 602. Accordingly, the housing 202 can be twisted to torque the helical fixation element 602 and screw the fixation element into the target tissue. By contrast, the pacing tip 411 of the pacing element 108 may include a nosecone 604. The nosecone 604 may, as described above, be coupled to the flexible conductor 406, e.g. by a bond or crimp. The nosecone 604 may have a conical distal end capable of puncturing tissue. Accordingly, the housing 202 can be pushed forward to cause the nosecone 604 to penetrate the target tissue and advance toward the target region.

Figure 7:
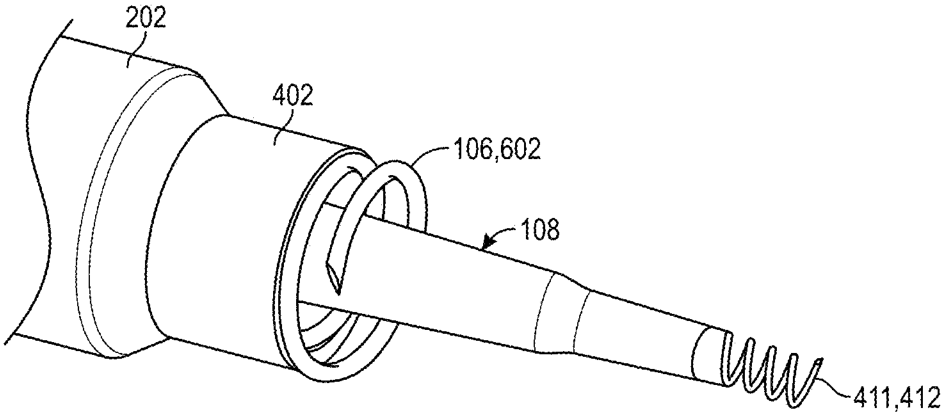
FIG. 7 is a perspective view of a distal portion of a biostimulator having a strain-relieved pacing element, in accordance with an embodiment.

Referring to FIG. 7, a perspective view of a distal portion of a biostimulator having a strain-relieved pacing element is shown in accordance with an embodiment. The pacing element 108 and the fixation element 106 may have a same mode of tissue penetration. In an embodiment, the fixation element 106 includes the helical fixation element 602. Similarly, the pacing tip 411 of the pacing element 108 may include the helical electrode 412. As described above, the helical electrode 412 can be coupled to the flexible conductor 406, e.g., by a bond or a crimp. Accordingly, the housing 202 can be rotated to screw the helical electrode 412 into the target tissue toward the target region. Similarly, when the helical fixation elements 602 has engaged the septal wall 110, the housing 202 may continue to be twisted to advance the helical fixation elements 602 into the target tissue.

Figure 8:
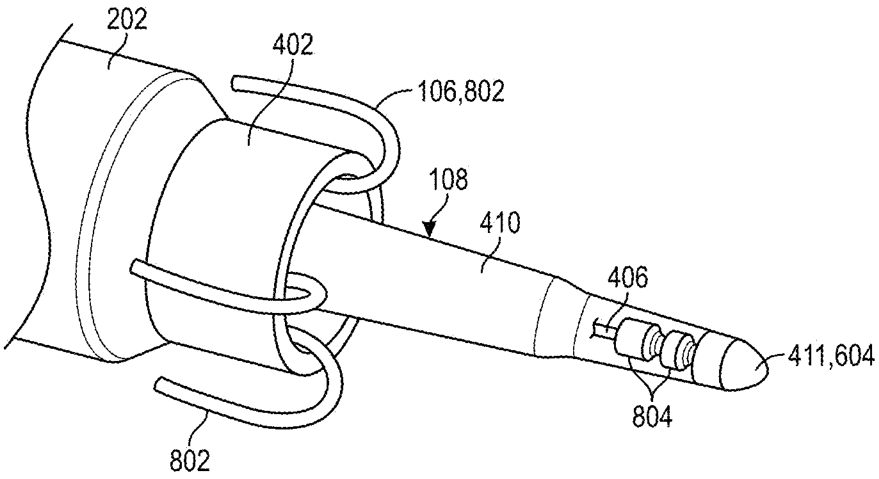
FIG. 8 is a perspective view of a distal portion of a biostimulator having a strain-relieved pacing element, in accordance with an embodiment.

Referring to FIG. 8, a perspective view of a distal portion of a biostimulator having a strain-relieved pacing element is shown in accordance with an embodiment. The fixation element 106 and the pacing element 108 may both be configured to plunge into the target tissue. For example, the pacing element 108 can include the nosecone 604, and the fixation element 106 can include several tines 802 configured to penetrate axially into the tissue. More particularly. The tines 802 may extend forward in a longitudinal direction when the tines 802 are in a biased state. When released from the biased state, the tines 802 can curl backward into U-shaped structures, as shown in FIG. 8. A longitudinal force can be applied to the proximal end of the housing 202, e.g., the attachment feature 210, to translate the pacing tip 411 and the tines 802 into the target tissue. A stiffness profile of the pacing element 108 is such that the pacing element 108 can penetrate the tissue without buckling of the strain relief 410. For example, the distally decreasing stiffness profile of the strain relief 410 can support the pacing element 108 against buckling, while allowing the pacing element 108 to flex under lateral loading. Accordingly, the nosecone 604 and the tines 802 can be pushed forward into the target tissue, and the tines 802 can then curl back to grab the tissue and fix the biostimulator in place. The tines 802 and the conical tip of the pacing element 108 can therefore engage the target tissue without rotating the housing 202 as required for the helical tip.

The tissue engagement mechanisms described above facilitate safe redeployment of the biostimulator in a ventricular septum 104. More particularly, the fixation element 106 and the pacing element 108 can be removed and redeployed several times as needed to achieve stable placement of the pacing tip at the target region. On average, it can take several attempts to position the tip correctly, and the helical or tined elements allow such redeployment to be performed safely. After each deployment, electrical measurements such as pacing capture threshold, impedance, R-wave measurements, paced QRS width, paced QRS morphology changes, or other parameters can be taken to verify suitable placement of the pacing tip. When the location is deemed suitable, the biostimulator can be fixed to the septum 104 by the fixation element 106. The pacing tip can therefore be located to deliver pacing impulses to the target region, and the biostimulator can be securely fastened within the heart chamber.

Still referring to FIG. 8, a partial cutaway view is used to reveal a section of the flexible conductor 406 within the strain relief 410. The flexible conductor 406 can include features to enhance a mechanical interaction between the pacing element components. For example, the flexible conductor 406 can include one or more radial protrusions 804. The radial protrusions 804 can be segments of the flexible conductor 406 having increased cross-sectional dimensions. More particularly, the radial protrusions 804 can be cylindrical segments having respective diameters, and segments of the flexible conductor proximal and distal to the cylindrical segments may have respective diameters that are smaller than the diameters of the radial protrusions 804. The radial protrusions 804 therefore create knobs to provide material for the strain relief 410 to grip. For example, the strain relief 410 can be formed into the recess between the radial protrusions 804 around the smaller diameter segment of the flexible conductor 406. The strain relief 410 between the radial protrusions 804 can interfere with the radial protrusions 804 when longitudinal loads are applied to the strain relief 410 outer surface 430. Accordingly, the radial protrusions 804 can secure the strain relief and resist relative movement between the strain relief 410 and the flexible conductor 406 or the pacing tip 411.

Figure 9:
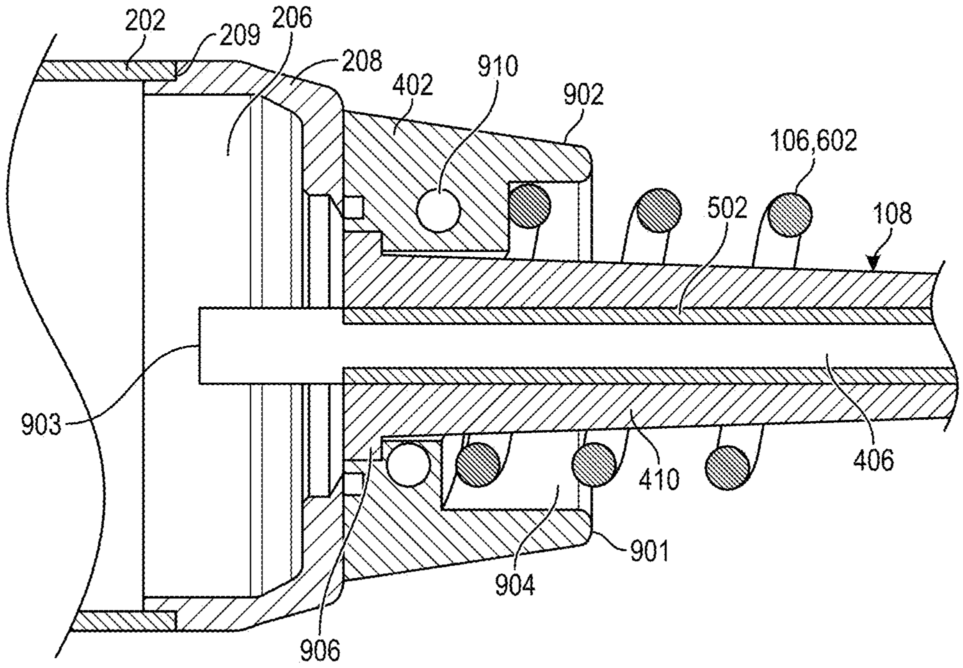
FIG. 9 is a cross-sectional view of a header assembly of a biostimulator, in accordance with an embodiment.

Referring to FIG. 9, a cross-sectional view of a header assembly of a biostimulator is shown in accordance with an embodiment. The fixation element mount 402 can be coupled to the housing 202. For example, the fixation element mount 402 can be secured to the flange 208, which may be attached to the distal housing end 209. The fixation element mount 402 may be press fit onto the flange 208, overmolded onto the flange 208, screwed onto the flange 208 using a threaded joint, bonded to the flange 208, etc. Similarly, the fixation element mount 402 may be attached to the distal end of the flange 208. In any case, the fixation element mount 402 can extend from the flange 208 to a distal mount end 901. In an embodiment, the fixation element mount 402 has an outer mount surface 902 extending from the flange 208 to the distal end of the fixation element mount 402. The outer mount surface 902 may be tapered. More particularly, an outer dimension, e.g., an outer diameter, of the outer mount surface 902 at the flange 208 may be larger than the outer dimension of the outer mount surface 902 at the distal mount end 901 of the fixation element mount 402.

The distal taper of the outer mount surface 902 can facilitate borrowing of the fixation element mount 402 into the target tissue. In an embodiment, the tapered outer mount surface 902 can be smooth. More particularly, there may be no ridges, threads, or recesses in the outer mount surface 902. The smooth surface can be flat between the proximal point at the flange 208 and the distalmost location at the distal mount end 901 of the fixation element mount 402. The flat and smooth surface can facilitate engagement of the fixation element mount 402 into the target tissue. Furthermore, the smooth surface may facilitate burrowing into the target tissue more easily than a ridged surface that would experience increased friction against the target tissue. A lead-in to the target tissue may be started by the pacing element 108 and the fixation element 106. The distal end of the fixation element mount 402 can locate within the lead-in and continue forward, wedging the target tissue outward as the tapered outer mount surface 902 progresses. Accordingly, the outer mount surface 902 can locate and secure the biostimulator within the target tissue.

The entry point into the target tissue formed by the fixation element 106 may be smaller than an outer dimension of the fixation element mount 402. For example, the fixation element 106 may include the helical fixation element 602 having a spiraling wire. Wire turns of the helical fixation element 602 can have an outer dimension, e.g., a major diameter. In an embodiment, the major diameter of the helical fixation element 602 is less than a diameter of the outer mount surface 902. The helical fixation element 602 may therefore be screwed into the target tissue to form an entry hole having a dimension similar to the major diameter. Thereafter, the fixation element mount 402 can engage the entry hole and wedge into the target tissue to secure the biostimulator within the tissue.

The pacing element 108, in addition to extending into the target tissue, can act as an electrical feedthrough. The flexible conductor 406 can include a proximal conductor end 903 located within the electronics compartment 206 of the housing 202. For example, the proximal conductor end 903 may be connected to circuitry within the electronics compartment 206. The electrical conductor can extend distally from the proximal conductor end 903 through the distal wall of the flange 208 and longitudinally into a space 904 within the fixation element mount 402. The space 904 can be a central channel of the fixation element mount 402 extending longitudinally through the fixation element mount 402 from a proximal end to a distal end of the fixation element mount 402. The central channel may be distal to the flange 208 and the housing 202. Accordingly, the electrical conductor can feed electrical signals from within the housing 202, through the flange 208, to a location distal to the housing 202.

In an embodiment, the strain relief 410 seals the space 904 between the fixation element mount 402 and the flexible conductor 406. More particularly, a portion of the space 904 can be located radially between an inner surface of the fixation element mount 402 and an outer surface of the flexible conductor 406. The portion of the space 904 can be an annular space. The tubular structure of the strain relief 410 can fit within the annular space and seal against the adjacent surfaces. More particularly, an outer surface of the strain relief 410 can press against the inner surface of the fixation element mount 402 and, similarly, the inner surface of the strain relief 410 can appose and/or press against the flexible conductor 406. Accordingly, the strain relief 410 can fill the space 904 and block ingress or egress of fluid between the electronics compartment 206 and the surrounding environment.

To further facilitate sealing between the strain relief 410 and the fixation element mount 402, the strain relief 410 may include a boot 906. The boot 906 can be a flange or lip portion of the strain relief 410 extending radially outward from the tubular structure. More particularly, the boot 906 can be a portion of the strain relief 410 having a larger diameter, e.g., a lip, which steps radially inward to the tapered outer surface 430 of the strain relief 410. The boot 906 can have a distal face that apposes and presses against a corresponding proximal-facing surface of the fixation element mount 402. Accordingly, the strain relief 410 can press and seal against the fixation element mount 402 to reduce a likelihood of ingress or egress of fluids between the electronics compartment 206 and the surrounding environment.

In an embodiment, the fixation element 106 is at least partly embedded in the fixation element mount 402. The fixation element 106 can include the helical fixation element 602, which has several turns. One or more turns of the helical fixation element 602 can be embedded in the fixation element mount 402. For example, the helical fixation element 602 can include a proximal turn 910, which can be a proximal most turn of the helix. The proximal turn 910 can be encased by a wall of the fixation element mount 402. More particularly, the proximal turn 910 can be radially inward of the tapered outer mount surface 902, e.g., between the outer mount surface 902 and the inner surface surrounding the space 904. The proximal turn 910 can be surrounded and encapsulated by the fixation element mount material. The fixation element 106 can extend longitudinally from the fixation element mount 402, e.g., helically about the longitudinal axis 204. Accordingly, the fixation element mount 402 can surround and secure a proximal portion of the fixation element 106, and the fixation element can extend distally beyond the fixation element mount 402 to engage the target tissue. The relationship between the fixation element 106 and the fixation element mount 402 is described in further detail below.

Figure 10:
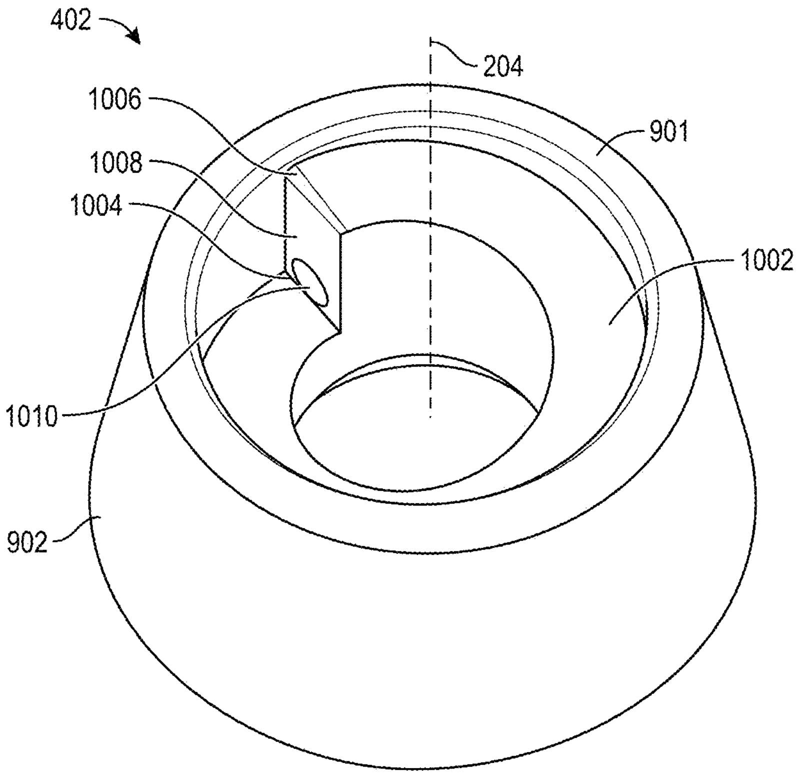
FIG. 10 is a perspective view of a fixation element mount, in accordance with an embodiment.

Referring to FIG. 10, a perspective view of a fixation element mount is shown in accordance with an embodiment. The fixation element mount 402 can be molded from a polymer, such as polyether ether ketone. The molded structure can include the outer mount surface 902 extending distally from a proximal edge of the fixation element mount 402 to the distal mount end 901 of the fixation element mount 402. In an embodiment, the fixation element mount 402 includes a spiral ramp 1002. Spiral ramp 1002 can be an internal feature of the fixation element mount 402. More particularly, the spiral ramp 1002 may be located within the space 904 radially inward from the outer mount surface 902. The spiral ramp 1002 can be defined by a spiral surface facing in the distal direction 404. The ramp can extend from a proximal ramp end 1004 to a distal ramp end 1006. Between the ends, the ramp surface can spiral about the longitudinal axis 204. In an embodiment, the spiral extends one full turn around the longitudinal axis 204. Accordingly, a longitudinal face 1008 of the inner surface of the fixation element mount 402 can extend in the longitudinal direction between the proximal ramp end 1004 and the distal ramp end 1006.

In an embodiment, the fixation element mount 402 includes a hole 1010 to receive the fixation element 106. The hole 1010 may be preformed in the fixation element mount 402 or by molding the fixation element mount 402 around the fixation element 106. For example, the fixation element mount 402 may be formed by overmolding the fixation element mount material around and onto the proximal turn 910 of the helical fixation element 602.

Figure 11:
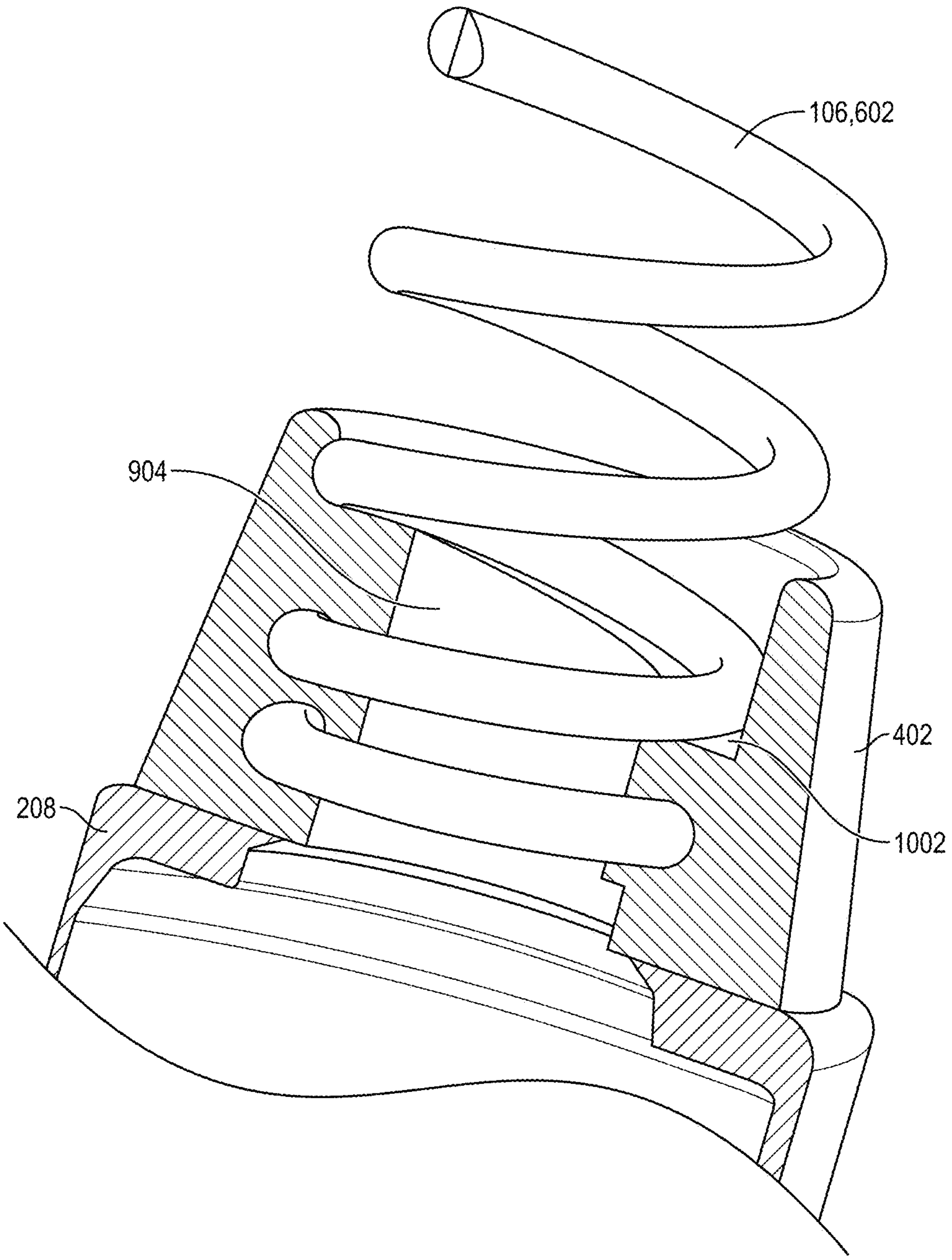
FIG. 11 is a cross-sectional perspective view of a fixation element mount assembly, in accordance with an embodiment.

Referring to FIG. 11, a cross-sectional perspective view of a fixation element mount assembly is shown in accordance with an embodiment. Whether the fixation element mount 402 is molded onto the fixation element 106 or the fixation element 106 is installed in the pre-molded fixation element mount 402 in a two-part assembly, the fixation element 106 can extend distally from within the fixation element mount 402 to a location distal to the fixation element mount 402. The fixation element 106 can extend along the spiral ramp 1002. For example, the helical fixation element 602 can extend from a location internal to the fixation element mount wall through the hole 1010 into the space 904. Within the space 904, at least one turn of the helical fixation element 602 can follow along the spiral ledge of the ramp. It will be appreciated that the ramp supports but does not fix the fixation element 106. Accordingly, the fixation element 106, when interfacing with tissue, can flex and move within the space 904 relative to the ramp. Rigid pinch points may be avoided, and tissue can conform into the crevices of the fixation element mount 402 without being pinched or injured.

The spiral ramp 1002 can have a width that is equal to or greater than a diameter of the wire forming the fixation element 106. The ramp can therefore fully support the fixation element 106, e.g., when a compressive load is applied to the helix. Furthermore, at least one turn can be embedded in the polymer of the fixation element mount 402. Thus, the fixation element mount 402 can strongly secure the proximal turns of the helical fixation element 602, and loosely support and allow for relative movement of medial turns of the helical fixation element 602. By contrast, the distal turns of the helical fixation element 602 may be distal to the fixation element mount 402 and therefore freely movable and engageable with the target tissue. The fixation element mount assembly provides a mechanism to flexibly engage the target tissue and secure the biostimulator thereto. The degree of freedom provided to the biostimulator during attachment to the tissue can, in combination with the flexibility of the pacing element 108, allow the biostimulator to securely engage the target region without traumatizing the septal wall 110.

Stiffness and fatigue resistance of the pacing element 108 are characteristics that may be correlated. More particularly, fatigue resistance of the flexible conductor 406 may be inversely correlated to stiffness of the flexible conductor 406. In several embodiments, fatigue resistance of the flexible conductor 406 may be improved by off-loading stiffness to another pacing element 108 component, e.g., the strain relief 410 that can include a stiffening element. For example, the pacing element 108 can include the stiffening element, such as a cable or a tubular braid as described below, to provide stiffness to the pacing element structure. Accordingly, the stiffening element may be stiffer than the flexible conductor 406 and provide column strength for the pacing element 108 while allowing the flexible conductor 406 to flex freely for good fatigue resistance.

Figure 12:
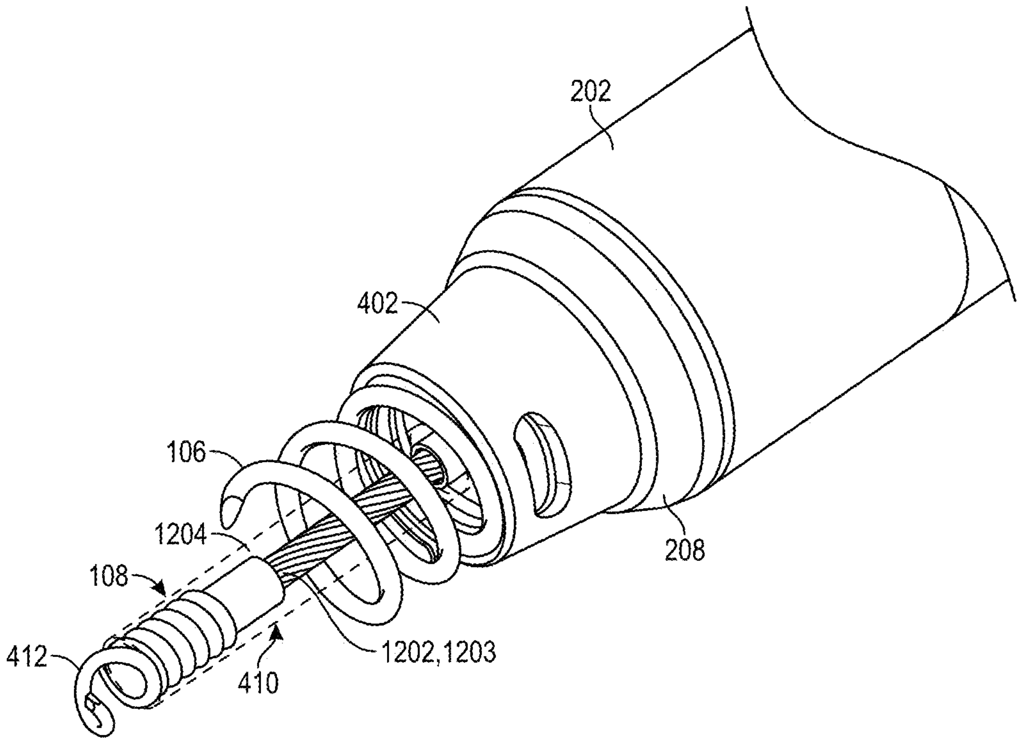
FIG. 12 is a perspective view of a distal portion of a biostimulator having a strain-relieved pacing element, in accordance with an embodiment.

Referring to FIG. 12, a perspective view of a distal portion of a biostimulator having a strain-relieved pacing element 108 is shown in accordance with an embodiment. The biostimulator structure incorporates elements similar to those described above, such as the fixation element 106 coupled to the housing 202 via the fixation element mount 402 and/or flange 208. Furthermore, the pacing element 108 can be coupled to the housing 202, and may include the helical electrode 412 to engage and deliver pacing impulses to the target tissue.

In an embodiment, the pacing element 108 includes the flexible conductor 406 (hidden) encapsulated within the strain relief 410. The strain relief 410 may, however, have a composite structure that includes a stiffening element 1202 physically separate from the flexible conductor 406. The stiffening element 1202 can include a cable 1203, e.g., a multi-stranded helical cable, extending around the flexible conductor 406. The stiffening element 1202 may be surrounded by an encapsulant 1204. For example, the encapsulant 1204 can include a polymer jacket that may be reflowed around the cable 1203 to form a composite structure. The composite structure includes the stiffening element 1202 encapsulated by the polymer jacket. The composite structure is described more with respect to FIG. 14, below. The composite structure can have a stiffness profile that, as described above, transitions such that a stiffness of the pacing element 108 and, in particular, the strain relief 410, decreases in a distal direction between the fixation element mount 402 and the helical electrode 412.

Figure 13:
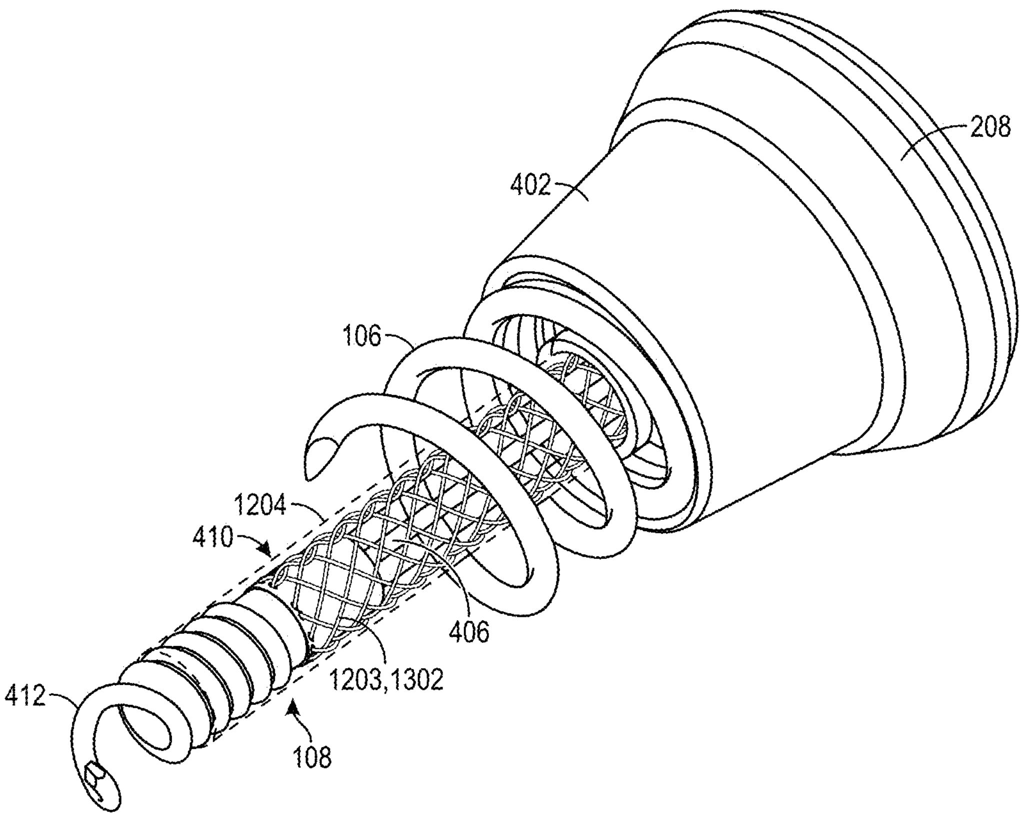
FIG. 13 is a perspective view of a distal portion of a biostimulator having a strain-relieved pacing element, in accordance with an embodiment.

Referring to FIG. 13, a perspective view of a distal portion of a biostimulator having a strain-relieved pacing element is shown in accordance with an embodiment. The biostimulator 100 structure incorporates elements similar to those described above, such as the fixation element 106 coupled to the housing 202 via the fixation element mount 402 and/or flange 208. Furthermore, the pacing element 108 can be coupled to the housing 202, and may include the helical electrode 412 to engage and deliver pacing impulses to the target tissue.

In an embodiment, the pacing element 108 includes the flexible conductor 406 encapsulated within the strain relief 410. The strain relief 410 may have a composite structure that includes a stiffening element 1202 physically separate from the flexible conductor 406. The stiffening element 1202 can include a tubular braid 1302, e.g., braided helical wires having openings between them, extending around the flexible conductor 406. More particularly, the tubular braid 1302 can include a braid lumen located centrally within the helically wound wires, and the flexible conductor 406 can extend longitudinally through the braid lumen. The stiffening element 1202 may be surrounded by an encapsulant 1204. For example, the encapsulant 1204 can include a polymer jacket that may be reflowed around the tubular braid 1302 to form a composite structure. The composite structure includes the stiffening element 1202 encapsulated by the polymer jacket. The composite structure is described more with respect to FIG. 15, below. The composite structure can have a stiffness profile that, as described above, transitions such that a stiffness of the pacing element 108 and, in particular, the strain relief 410, decreases in a distal direction between the fixation element mount 402 and the helical electrode 412.

Figure 14:
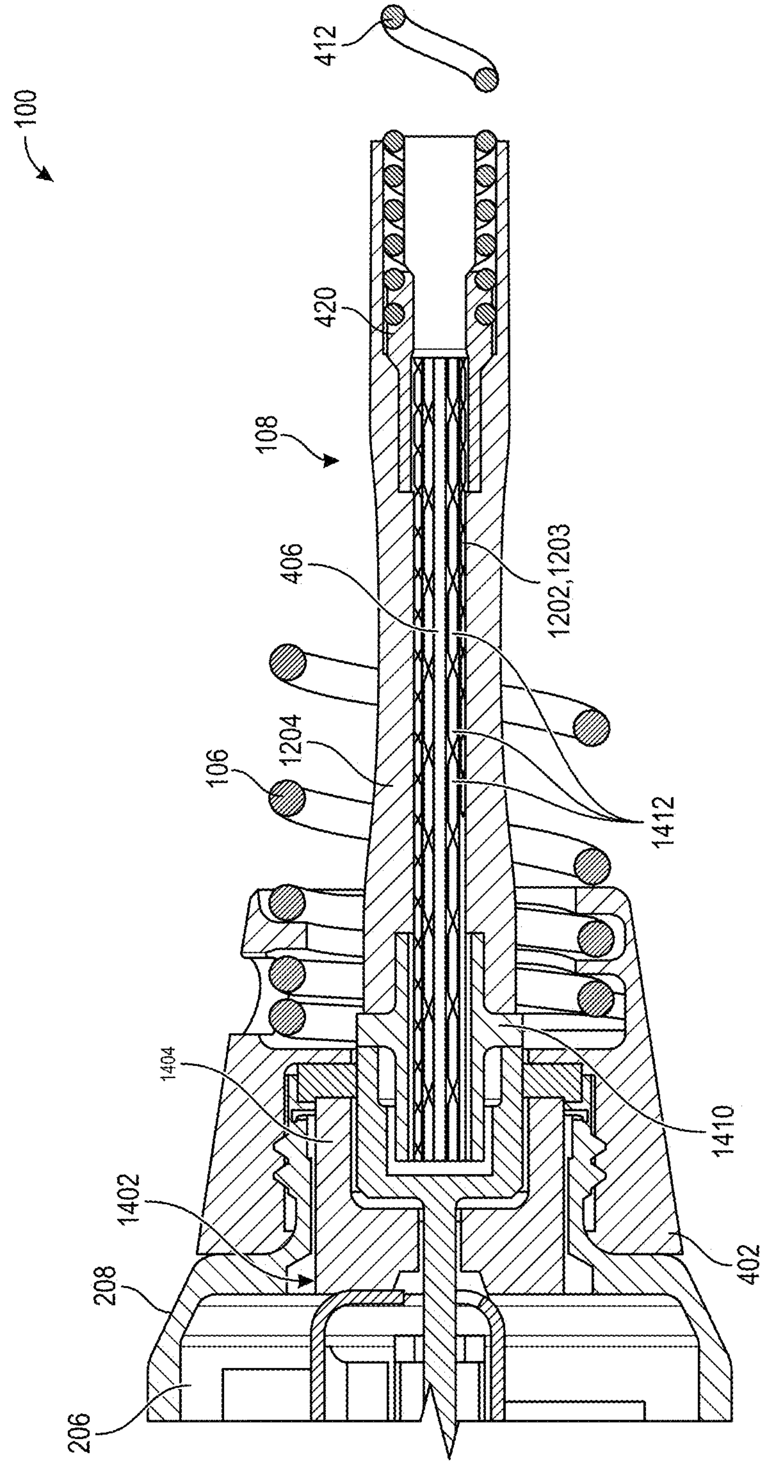
FIG. 14 is a cross-sectional view of a header assembly of a biostimulator, in accordance with an embodiment.

Referring to FIG. 14, a cross-sectional view of a header assembly of a biostimulator is shown in accordance with an embodiment. The biostimulator 100 can include an electrical feedthrough 1402 to communicate electrical signals from circuitry within the electronics compartment 206, proximal to the flange 208, to the pacing element 108 distal to the flange 208. The electrical feedthrough 1402 can physically separate the electronics compartment 206 from a surrounding environment. The electrical feedthrough 1402 can include an insulator 1404 separating an electrode pin 1406 from the flange 208. The electrical signals can travel through the insulator 1404 to the pacing element 108 that is supported, e.g., by a cup or other end structure of the electrode pin 1406. The support may provide a stable base for the pacing element 108, e.g., about which the pacing element 108 may flex or bend as a cantilever. Accordingly, the electrical feedthrough 1402 can both isolate the electronics compartment 206 to improve corrosion resistance of the biostimulator 100, and provide a stable support to improve fatigue resistance of the pacing element 108.

The pacing element 108 can include a ferrule 1410 to join the flexible conductor 406 to the electrode pin 1406. The ferrule 1410 may be an annular structure, for example, having a proximal portion that fits into the cup. A lip of the ferrule 1410 can interface with a distal end of the cup and, in an embodiment, may be welded or otherwise attached to the cup to form an electrical pathway from the electrode pin 1406 into the ferrule 1410.

In an embodiment, the flexible conductor 406, or an intermediate conductive structure in contact with the flexible conductor 406, can be mechanically constrained by the ferrule 1410. For example, the stiffening element 1202 can surround the flexible conductor 406, and the ferrule 1410 can be crimped onto the stiffening element 1202. The stiffening element 1202 may be a cable 1203 having several cable strands 1412 extending helically about the flexible conductor 406. More particularly, the flexible conductor 406 can be a longitudinally extending wire that is centrally located within the helical strands 1412 of the cable 1203. Accordingly, the radial force applied to the cable 1203 by the crimped ferrule 1410 can clamp the strands 1412 onto the flexible conductor 406. Electrical signals may therefore pass from the electrode pin 1406 through the ferrule 1410 and the cable 1203 to the flexible conductor 406.

The flexible conductor 406 and the stiffening element 1202 can extend longitudinally from the electrode pin 1406 to the tip support 420. In an embodiment, the tip support 420 includes an internal channel to receive the flexible conductor 406 and the stiffening element 1202. For example, distal ends of the cable 1203 and/or the flexible conductor 406 wire can be inserted into the internal channel. The tip support 420 may then be physically and electrically connected to the conductive structures via a weld, crimp, or another bond. As described above, the tip support 420 can support the helical electrode 412, and may be electrically connected to the helical electrode 412. Accordingly, electrical signals may pass from circuitry within the electronics compartment 206 to the target tissue via an electrical pathway passing through the electrode pin 1406, the ferrule 1410, the cable 1203, the flexible conductor 406, the tip support 420, and the helical electrode 412.

As described above, the flexible conductor 406 can be a thin wire or cable extending longitudinally and, thus, may be substantially flexible and bendable. The stiffening element 1202 may, on the other hand, be configured to have more axial and lateral stiffness than the flexible conductor 406. A material and size of the helical strands 1412 may be configured to achieve such relative rigidity. For example, the helical strands 1412 may be formed from wires that are thicker than the flexible conductor 406. A number of strands 1412 and a pitch of the strands 1412 may also be selected to provide higher column strength and lateral stiffness than the flexible conductor 406. The cable 1203 may, therefore, contribute stiffness to the pacing element 108 while allowing the flexible conductor 406 to remain highly flexible for excellent fatigue resistance.

The helical strands 1412 can also facilitate the stiffness profile that decreases in the distal direction. For example, the number and pitch of the strands, and/or the material or size of the strands can be tuned such that the stiffening element 1202 has a stiffness that decreases distally between the ferrule 410 and the tip support 420. By way of example, the pitch of the strands may increase in a distal direction to result in a decreasing stiffness in the distal direction. The stiffening element 1202 and encapsulant 1204 can have stiffnesses that combine to provide a composite stiffness of the pacing element 108. In an embodiment, the composite stiffness decreases in the distal direction.

In an embodiment, the pacing element 108 includes the encapsulant 1204 surrounding the cable 1203. The encapsulant 1204 may be a polymer jacket or sheath that extends longitudinally over the cable 1203 between the ferrule 1410 and the tip support 420. For example, the encapsulant 1204 can include a tubular structure extending from a proximal tube end on the ferrule 1410 to a distal tube end on the tip support 420. The encapsulant 1204 can electrically insulate the cable 1203 from the surrounding environment. It will be appreciated that the distally decreasing stiffness profile of the pacing element 108 can be achieved without tapering an outer surface of the encapsulant 1204 consistently in the distal direction. The composite stiffness may be driven by the stiffness transition of the encapsulated stiffening element 1202. Accordingly, the outer surface can be straight (cylindrical), concave, etc.

The tubular structure of the encapsulant 1204 may be subjected to a heat reflowing process during manufacturing to cause the tube to conform to outer surfaces of the underlying structures, e.g., the ferrule 1410, the cable 1203, the tip support 420, and the helical electrode 412. As illustrated, a wall thickness of the encapsulant 1204 may vary over a length. For example, the encapsulant wall thickness may be greater near the proximal tube end and the distal tube end than at a middle of the tube. The wall thickness variation can result from material compression during the reflowing process, which can be applied by a removable heat shrink jacket, for example. It will be appreciated that the wall thickness variation can make the middle more flexible and contribute to the overall flexibility of the pacing element 108, which nonetheless has stable ends due to the larger wall thickness at the end locations. Notably, the strain relief 410 can taper in one or both of the distal direction or a proximal direction. Accordingly, in addition to electrically insulating the cable 1203 and flexible conductor 406, the encapsulant 1204 can tune the flexibility of the pacing element 108 to be more flexible near the middle of the pacing element 108 than near the ends.

Similar benefits, e.g., tuned distally-decreasing stiffness and good fatigue resistance, can be achieved using alternative composite structures for the pacing element 108. For example, as described below, the composite structure can include a stiffening element 1202 having a tubular braid 1302 to stiffen the pacing element 108 and support a highly flexible and fatigue resistant flexible conductor 406.

Figure 15:
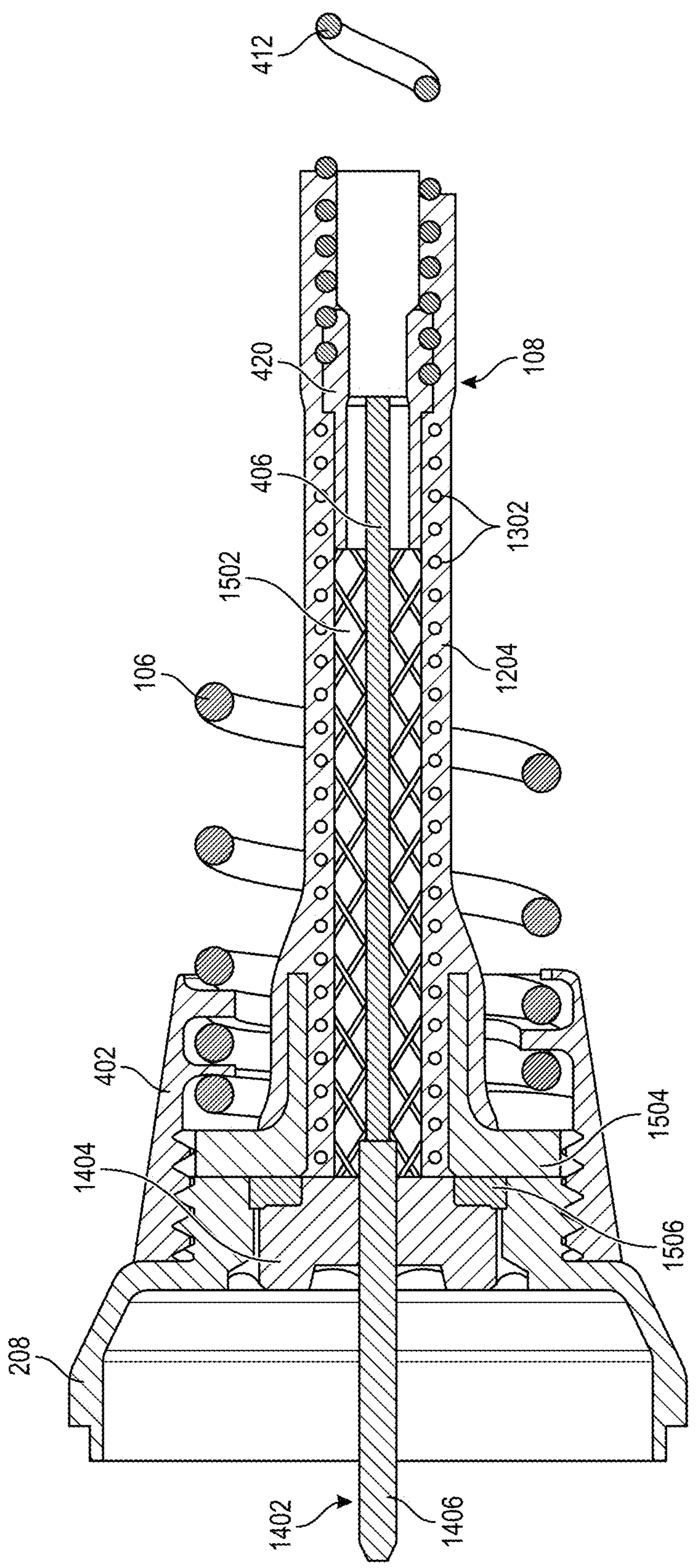
FIG. 15 is a cross-sectional view of a header assembly of a biostimulator, in accordance with an embodiment.

Referring to FIG. 15, a cross-sectional view of a header assembly of a biostimulator is shown in accordance with an embodiment. The biostimulator 100 can include the electrical feedthrough 1402 mounted within the flange 208 to communicate electrical signals from circuitry within the electronics compartment 206. The electrical feedthrough 1402 may, as described above, have the electrode pin 1406 extending through the insulator 1404. The insulator 1404 can electrically insulate the electrode pin 1406 from the flange 208.

In an embodiment, the electrode pin 1406 is directly connected to the flexible conductor 406. For example, the flexible conductor 406 can be a thin wire or cable 1203 having a proximal conductor end attached directly to the electrode pin 1406, e.g., by a weld, as opposed to indirectly through a crimped ferrule 1410. Electrical signals may pass from the electrode pin 1406 through the flexible conductor 406. Furthermore, the flexible conductor 406 may be connected to the tip support 420, which may support the helical electrode 412. Accordingly, pacing impulses can travel via an electrical pathway through the electrode pin 1406, the flexible conductor 406, the tip support 420, and the helical electrode 412.

The biostimulator 100 can include the stiffening element 1202 having a composite structure including the encapsulant 1204 and the tubular braid 1302. More particularly, the tubular braid 1302 can be encapsulated by the encapsulant 1204. The encapsulant 1204 may effectively form a tubular matrix of encapsulant material surrounding the tubular braid 1302. The tubular matrix can have an inner surface extending around a braid lumen 1502, and an outer surface facing radially outward, e.g., toward the fixation element 106.

The flexible conductor 406 can extend longitudinally through the braid lumen 1502 The flexible conductor 406 may be a thin wire, e.g., a wire coated with a fluorine-based plastic, such as ethylene tetrafluoroethylene (ETFE). An annular gap may be located between the encapsulant 1204 and/or tubular braid 1302 and the flexible conductor 406. Accordingly, the flexible conductor 406 may be physically decoupled and spaced apart from the encapsulant 1204 by an air gap. Alternatively, the encapsulant 1204 can fill the braid lumen 1502 and conform to an outer surface of the flexible conductor 406. In either case, the composite structure of the stiffening element 1202 can be stiffer than the flexible conductor, allowing the flexible conductor 406 to have high flexibility and fatigue resistance.

The pacing element 108 may be coupled to the flange 208 via a stiffener 1504. The stiffener 1504 can be, for example, a tubular structure having sections with different outer diameters. The tubular structure may be formed from a material or have a size and shape that makes the proximal end of the pacing element 108 more rigid than a middle of the pacing element 108. For example, the stiffener 1504 may be formed from PEEK or a metal.

A proximal portion of the stiffener 1504 can project laterally outward to form a lip having an outer dimension that is greater than a major diameter of a threaded portion of the flange 208. By contrast, a distal section of the stiffener 1504 can have an outer dimension that is smaller than the major diameter. The thinner distal section can provide an anchor point for the encapsulant 1204. More particularly, the encapsulant 1204 can be reflowed over and around the distal section during a manufacturing process. The encapsulant 1204 may also be located radially within a channel of the stiffener 1504. Accordingly, the distal section can be sandwiched between and held by portions of the encapsulant 1204. The stiffener 1504 may therefore form a stiff proximal section of the pacing element 108.

The stiff proximal section provided by the stiffener 1504 can lock the braided body of the composite stiffening element 1202 to the flange 208. The proximal portion of the stiffener 1504 can be sandwiched between a distal end of the flange 208 and the fixation element mount 402. More particularly, the fixation element mount 402 may be engaged with, e.g., threaded onto, the flange 208 and the stiffener 1504 may be longitudinally trapped and clamped between the threaded components. The pacing element 108 can accordingly become locked to the fixation element mount 402 and the flange 208.

In an embodiment, an epoxy backfill 1506 can be flowed into or otherwise disposed in a gap between the insulator 1404, the stiffener 1504, and the flange 208. The epoxy backfill 1506 can fill the gap to form a hermetic seal between the components at the backfilled location. More particularly, fluid passage into the gap may be limited by the epoxy filler and, thus, corrosion resistance of the header assembly may be enhanced.

The tubular braid 1302 may contribute a majority of stiffness to the pacing element 108. More particularly, the braid material may be stiffer than the flexible conductor 406 or the encapsulant 1204. Accordingly, the braid characteristics can be selected to tailor the column strength and/or bending stiffness of the pacing element 108. Such characteristics can include a wire material, a pic count of the braid, a wire size, etc. Such braid characteristics may be tuned to provide a distally-decreasing stiffness profile to the tubular braid 1302 and the pacing element 108. For example, the pic count may be higher in a proximal section of the tubular braid than a distal section of the tubular braid to decrease the amount of braid material, and thus stiffness, of the stiffening element in the distal direction. In an embodiment, to a lesser degree, the encapsulant material may also be selected to provide a composite structure that is stiffer than the flexible conductor 406. For example, the encapsulant may be formed from materials of varying hardness and/or tapering outer surfaces to provide a distally-decreasing stiffness. Tissue penetration and fatigue resistance of the pacing element 108 can be enhanced accordingly.

Figure 16:
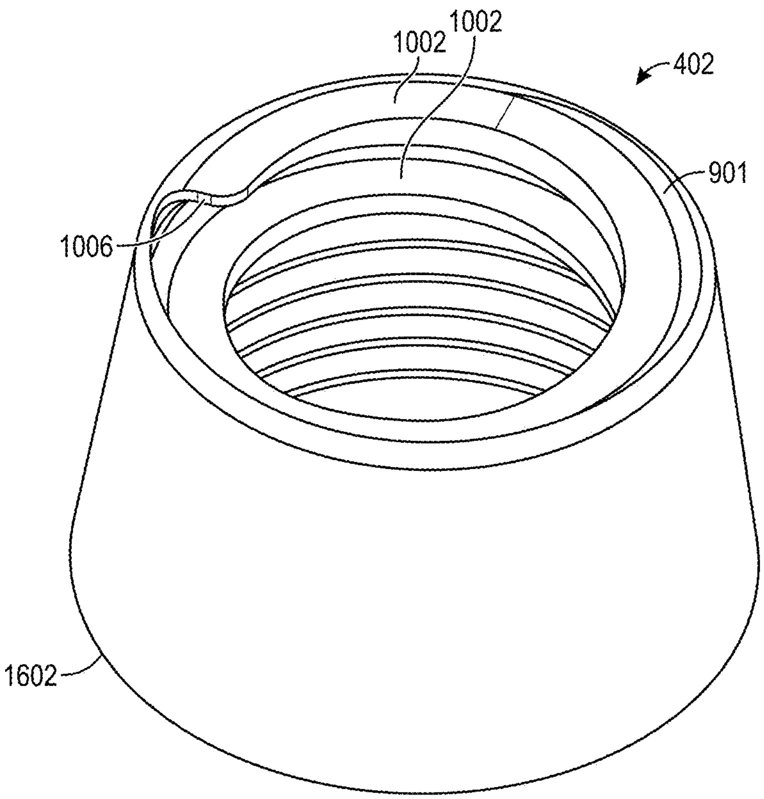
FIG. 16 is a perspective view of a fixation element mount of a biostimulator, in accordance with an embodiment.

Referring to FIG. 16, a perspective view of a fixation element mount of a biostimulator is shown in accordance with an embodiment. As described above, the fixation element mount 402 can have a tapered outer surface. More particularly, the outer surface of the fixation element mount 402 can taper radially inward from a proximal mount end 1602 to a distal mount end 901. Furthermore, the fixation element mount 402 can include the spiral ramp 1002 extending from the distal ramp end 1006 about a central axis over one or more turns. The spiral ramp 1002 can receive the fixation element 106 to secure and support the fixation element 106 within a central channel of the fixation element mount 402. Accordingly, a proximal portion of the fixation element 106 received within the central channel can be isolated from surrounding tissue that the tapered outer surface engages during implant.

Figure 17:
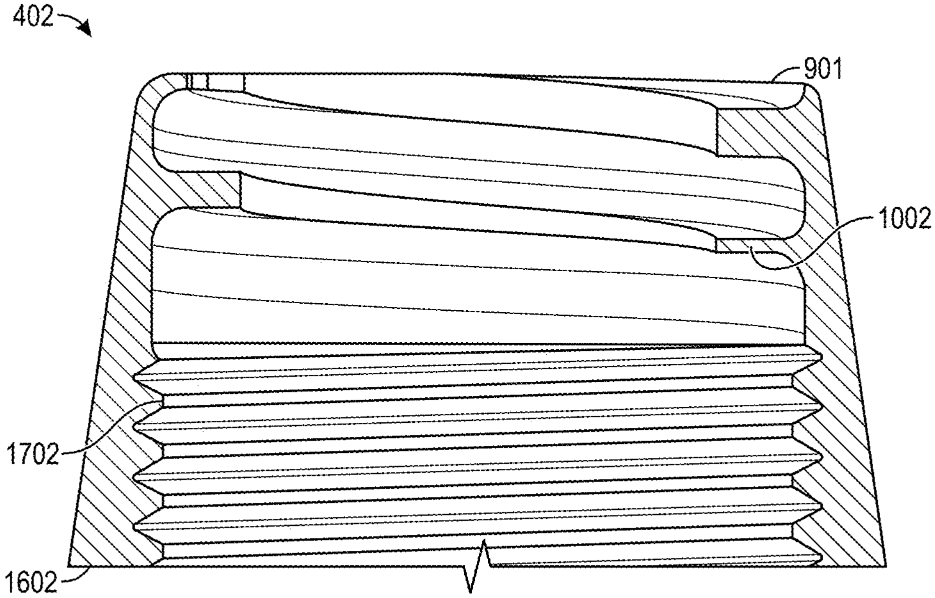
FIG. 17 is a cross-sectional view of a fixation element mount of a biostimulator, in accordance with an embodiment.

Referring to FIG. 17, a cross-sectional view of a fixation element mount of a biostimulator is shown in accordance with an embodiment. The fixation element mount 402 can include an internal thread 1702 extending about the central axis. The internal thread 1702 can be milled to match an external thread of the flange 208. Accordingly, the fixation element mount 402 can be screwed onto the flange 208, as described above, to capture and clamp the stiffener 1504 between a spiral ramp 1002 that receives the fixation element 106 and the distal end of the flange 208. Similarly, the fixation element 106 on the spiral ramp 1002 may be squeezed against the stiffener 1504. Accordingly, it will be appreciated that the fixation element 106 may be secured between the fixation element mount 402 and the flange 208 with or without fully embedding (encapsulating) the fixation element 106 in the fixation element mount 402, as described above.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
- a housing having a longitudinal axis and containing an electronics compartment;
- a fixation element coupled to the housing, wherein the fixation element extends about the longitudinal axis; and
- a pacing element coupled to the housing, wherein the pacing element includes a strain relief including a tubular braid having a braid lumen, a tip support having an internal channel, a flexible conductor extending longitudinally through the braid lumen into the internal channel of the tip support within the braid lumen, and a distal pacing tip mounted on the tip support.

2. The biostimulator of claim 1, wherein the flexible conductor includes a conductive cable.

3. The biostimulator of claim 1, wherein the fixation element includes a helical fixation element.

4. The biostimulator of claim 1, wherein the fixation element includes a plurality of tines.

5. The biostimulator of claim 1, wherein the distal pacing tip includes a nosecone.

6. The biostimulator of claim 1, wherein the distal pacing tip includes a helical electrode.

7. The biostimulator of claim 1, further comprising a fixation element mount coupled to the housing, wherein the fixation element mount has a tapered outer mount surface.

8. The biostimulator of claim 7, wherein the fixation element is at least partly embedded in the fixation element mount.

9. The biostimulator of claim 8, wherein the fixation element includes a helical fixation element having one or more turns embedded in the fixation element mount.

10. The biostimulator of claim 7, wherein the fixation element mount includes a spiral ramp, and wherein the fixation element extends along the spiral ramp.

11. The biostimulator of claim 1, wherein the flexible conductor includes one or more radial protrusions to grip the strain relief.

12. A biostimulator, comprising:
- a housing having a longitudinal axis and containing an electronics compartment; and
- a pacing element coupled to the housing, wherein the pacing element includes a strain relief including a tubular braid having a braid lumen, a tip support having an internal channel, a flexible conductor extending longitudinally through the braid lumen into the internal channel of the tip support within the braid lumen, and a distal pacing tip mounted on the tip support.

13. The biostimulator of claim 12, wherein the flexible conductor includes a conductive cable.

14. The biostimulator of claim 12, wherein the distal pacing tip includes a helical electrode.

15. A biostimulator, comprising:
- a housing having a longitudinal axis and containing an electronics compartment;

a fixation element mount coupled to the housing, wherein the fixation element mount has a tapered outer mount surface, and wherein the tapered outer mount surface continuously tapers from a proximal mount end to a distal mount end of the fixation element mount; and a fixation element partly embedded in the fixation element mount radially inward of the tapered outer mount surface, wherein the fixation element extends helically about the longitudinal axis.

16. The biostimulator of claim 15, wherein the fixation element includes a helical fixation element having one or more turns embedded in the fixation element mount.

17. The biostimulator of claim 15, wherein the fixation element mount includes a spiral ramp, and wherein the fixation element extends along the spiral ramp.

18. The biostimulator of claim 15, wherein a strain relief seals a space between the fixation element mount and a flexible conductor.

* * * * *